US00PP09773P

United States Patent [19]

Utecht

[11] Patent Number: Plant 9,773

[45] Date of Patent: Dec. 31, 1996

[54] GERANIUM PLANT NAMED 'FISMEGA'

[75] Inventor: Angelika Utecht, Montabaur, Germany

[73] Assignee: Florfis AG, Binningen, Switzerland

[21] Appl. No.: 518,894

[22] Filed: Aug. 29, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fismega, characterized by its intense salmon orange flower color, large single flowers, large umbels which are free standing above the foliage, dark green leaves with narrow zonation, and medium tall plant habit.

1 Drawing Sheet

The present invention comprises a new and distinct cultivar of geranium, botanically known as *Pelargonium zonale*, and hereinafter referred to by the cultivar name Fismega.

Fismega is a product of planned breeding program which had the objective of creating new geranium cultivars with single flowers in various colors, dark green foliage and good cultivation ability.

Fismega was originated from a hybridization made by the inventor Angelika Utecht in a controlled breeding program in Hillscheid, Germany, in Summer 1990.

The female parent was an unnamed seedling characterized by single salmon pink flowers and dark green, only slightly zoned foliage. It was derived from crosses in a breeding program involving the cultivar Dresdner Puppe Rosa, characterized by light pink flowers with dark pink eyes; a tetraploid line of Stadt Bern, with single orange-red flowers and dark green strongly zoned foliage, and Bianca which has single white flowers in combination with light green foliage.

The male parent of Fismega was also an unnamed seedling, characterized by light salmon semi-double flowers and medium green foliage with strong zonation. It was originated from crosses between the vigorously growing, salmon colored cultivar Springtime Irene, a tetraploid line of Stadt Bern, and the salmon pink colored, medium sized variety Palais, disclosed in U.S. Plant Pat. No. 5,315, which is marketed under the trademark "Pink Expectations".

Fismega was discovered and selected as one flowering plant within the progeny of the stated cross by Angelika Utecht in 1991 in a controlled environment in Galdar, Gran Canaria, Spain.

The first act of asexual reproduction of Fismega was accomplished when vegetative cuttings were taken from the initial selection in Jun. 1991 in a controlled environment in Galdar, Gran Canaria, Spain, by, or under the supervision of the inventor.

Horticultural examination of plants grown from these cuttings initiated in May 1992 in Hillscheid, Germany, and continuing thereafter, has demonstrated that the combination of characteristics as herein disclosed for Fismega are firmly fixed and are retained through successive generations of asexual reproduction.

Fismega has not been observed under all possible environmental conditions. The phenotype may vary significantly with variations in environment such as temperature, light intensity and day length, without, however, any variance in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fismega, which in combination distinguish this geranium as a new and distinct cultivar:

1. Large single flowers
2. Intense salmon flower color, with little tendency to fading
3. Semi-spherically shaped umbals which are well above the foliage
4. Dark green foliage with narrow, ring-shaped zonation
5. Medium tall, well branched plant habit
6. Medium to late spring flower response Of the many commercial cultivars known to the present inventor, the most similar in comparison to Fismega is the commercial variety Claire, disclosed in U.S. Plant Pat. No. 7,153 under the varietal designation Marktex. In general comparison to Claire, Fismega has a more intense salmon flower color (R.H.S. 43 B/C) than Claire (R.H.S. 43 C/D) and somewhat darker green foliage. Plant habit and zonation are similar.

The accompanying photographic drawing is a top perspective view which shows typical flower and foliage characteristics of Fismega, with colors being as true as possible with illustrations of this type.

In the following description color references are made to The Royal Horticultural Society Colour Chart. The color values were determined outdoors from flowers taken from plants grown in greenhouse in May 1994 in Hillscheid, Germany.

Classification:

*Botanical.*—A hybrid of the species *Pelargonium zonale* 1'Hert.

*Commercial.*—Zonal geranium, cv. Fismega.

INFLORESCENCE

A. Umbel:

*Shape.*—Semi-spherical.
*Average diameter.*—115 mm.
*Average depth.*—65 mm.
*Peduncle length.*—135 mm.
*Peduncle color.*—Dark red.
*Pedicel length.*—20 mm.
*Pedicel color.*—Light to dark red.
*Number of open flowers per umbel.*—24.

B. Corolla:

*Average diameter.*—43 mm.
*Form.*—Single.
*Number of petals.*—5.
*Number of petaloids.*—0.
*Color (general tonality from a distance of three meters.*—Salmon orange.

*Color of upper surface of petals.*—43 B–C.
*Markings.*—Short light red veins at the base of upper petals.
*Color of lower surface of petals.*—44 D.
*Color of sepals.*—Light green, red at the base.
*Number of sepals.*—5.

C. Bud:
*Shape.*—Elliptical.
*Color (adaxial).*—Light green, red at the base.
*Color (abaxial).*—Orange to orange red.

D. Reproductive organs:
*Androecium.*—7 fertile anthers, white and salmon filaments, yellow-orange pollen.
*Gynoecium.*—5–6 lobed stigma, salmon style and stigma.
*Seed.*—May show spontaneous seed set.

E. Spring flowering response period: In Hillscheid, Germany, in 1994 plants of Fismega had an average 0.5 umbels with at least one flower opened 11 weeks after planting of unrooted cuttings.

F. Outdoor flower production: The flower count in 1994 in Hillscheid, Germany, indicated about 25 umbels per plant for May through August observation period.

G. Durability: Shatter resistance average for a single flowered variety; good rain resistance.

PLANT

A. Foliage:
*Form.*—Kidney-shaped.
*Margin.*—Bicrenate.
*Size of leaf.*—105 mm.
*Color of upper surface.*—Medium to dark green, 137 C.
*Color of zonation.*—Brown, wide narrow ring 166A.
*Tolerance of botrytis.*—Average.

B. General appearance and form:
*Internode length.*—5–10 mm.
*Branching pattern.*—1.8 branches.
*Height of plants.*—28 cm (in June, 16-week-old plants).

C. Ploidy: Tetraploid.

I claim:

1. It is claimed a new and distinct cultivar of geranium plant named Fismega as illustrated and described.

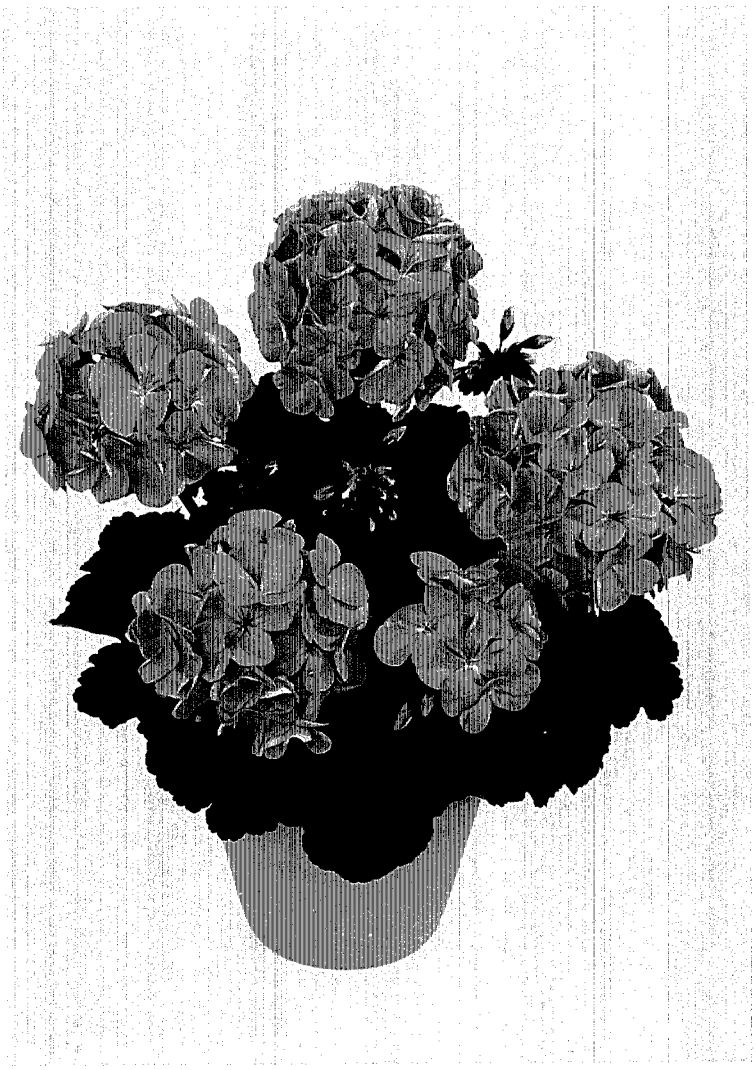

* * * * *